United States Patent
Hösel et al.

(10) Patent No.: US 7,173,703 B2
(45) Date of Patent: Feb. 6, 2007

(54) APPARATUS ON A TEXTILE FIBRE PROCESSING MACHINE FOR EVALUATING TEXTILE FIBRE MATERIAL

(75) Inventors: Fritz Hösel, Mönchengladbach (DE); Guido Engels, Rommerskirchen (DE)

(73) Assignee: Trutzschler GmbH & Co. KG, Monchengladbach (DE)

( * ) Notice: Subject to any disclaimer, the term of this patent is extended or adjusted under 35 U.S.C. 154(b) by 303 days.

(21) Appl. No.: 10/602,046

(22) Filed: Jun. 24, 2003

(65) Prior Publication Data
US 2004/0012786 A1    Jan. 22, 2004

(30) Foreign Application Priority Data
Jul. 20, 2002    (DE)    ............... 102 33 011

(51) Int. Cl.
*G01N 21/84*    (2006.01)
(52) U.S. Cl. ..................... 356/429; 356/460
(58) Field of Classification Search ............ 356/429, 356/430, 238.2, 238.3; 19/98–107
See application file for complete search history.

(56) References Cited

U.S. PATENT DOCUMENTS

| | | | | | |
|---|---|---|---|---|---|
| 4,187,584 | A | * | 2/1980 | Trutzschler | .............. 19/81 |
| 4,676,651 | A | * | 6/1987 | Beckstein | ............... 356/429 |
| 4,686,744 | A | * | 8/1987 | Shofner | ................ 19/105 |
| 4,827,781 | A | * | 5/1989 | Vollm | ................. 73/864.41 |
| 4,885,709 | A | * | 12/1989 | Edgar et al. | ............ 356/432 |
| 4,974,296 | A | * | 12/1990 | Vidler | .................. 19/239 |
| 5,130,559 | A | * | 7/1992 | Leifeld et al. | ........ 250/559.11 |
| 5,295,401 | A | * | 3/1994 | Toedtli | ................ 73/863.92 |
| 5,469,253 | A | * | 11/1995 | Shofner et al. | ........ 356/238.3 |
| 5,499,794 | A | * | 3/1996 | Aeppli | ................ 356/430 |
| 5,533,145 | A | * | 7/1996 | Shofner et al. | ............ 382/141 |
| 5,539,515 | A | * | 7/1996 | Shofner et al. | ........ 356/238.3 |
| 5,544,090 | A | * | 8/1996 | Shofner et al. | ........... 356/430 |
| 5,626,237 | A | * | 5/1997 | Hergeth | ................ 209/580 |
| 5,642,553 | A | * | 7/1997 | Leifeld | ................... 19/98 |
| 5,692,267 | A | * | 12/1997 | Leifeld | .................. 19/106 R |
| 5,791,489 | A | | 8/1998 | Leifeld | |
| 5,930,870 | A | * | 8/1999 | Leifeld et al. | ............. 19/105 |
| 6,477,741 | B2 | * | 11/2002 | Hosel | ................ 19/107 |
| 6,611,994 | B2 | * | 9/2003 | Bischofberger et al. | ....... 19/98 |
| 6,647,595 | B2 | * | 11/2003 | Schurenkramer et al. | . 19/106 R |

(Continued)

FOREIGN PATENT DOCUMENTS

DE    39 26 346 A1    2/1991

(Continued)

*Primary Examiner*—Michael P. Stafira
*Assistant Examiner*—Juan D Valentin, II
(74) *Attorney, Agent, or Firm*—Venable LLP; Robert Kinberg; Steven J. Schwarz

(57) ABSTRACT

In an apparatus for inspecting and evaluating fiber material, for example a sliver or fleece, an opto-electronic system, is provided across the width of a textile machine and scans the moving fiber material and converts the measured values into electronic signals. The system is in communication with an image-evaluating device which evaluates the raw data of the system. In order to produce an apparatus that is space-saving and permits a lower overall height combined with at least the same image quality, three or more imaging devices are provided side by side and, in relation to the unit of width, the number of cameras increases as the distance between objective and fiber sliver decreases.

23 Claims, 17 Drawing Sheets

U.S. PATENT DOCUMENTS 6,848,149 B1 * 2/2005 Baechler .................... 19/65 R

FOREIGN PATENT DOCUMENTS

| | | |
|---|---|---|
| DE | 39 28 279 A1 | 2/1991 |
| DE | 693 29 185 T2 | 7/1994 |
| DE | 44 15 959 A1 | 11/1995 |
| DE | 196 04 499 A1 | 10/1996 |
| DE | 196 24 905 A1 | 1/1998 |
| DE | 199 30 154 A1 | 1/2001 |
| DE | 102 33 011 A1 | 1/2004 |
| EP | 0 606 626 B1 | 7/1994 |
| EP | 1 249 530 A3 | 10/2002 |
| GB | 1 217 642 | 12/1970 |
| GB | 1 422 861 | 1/1976 |
| GB | 2 300 004 A | 10/1996 |
| GB | 2 377 713 A | 1/2003 |
| WO | WO 02/068740 A1 | 9/2002 |

* cited by examiner

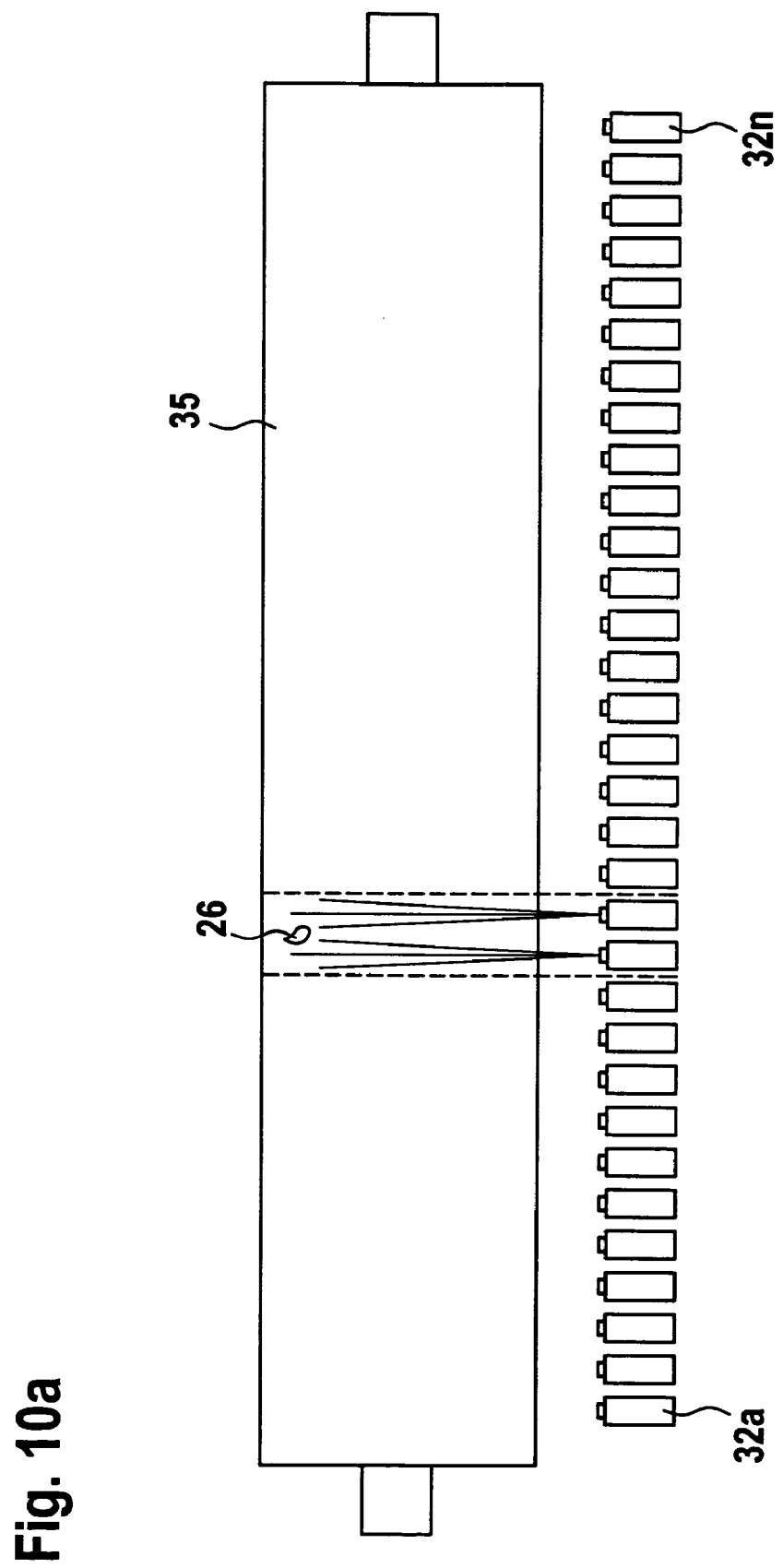

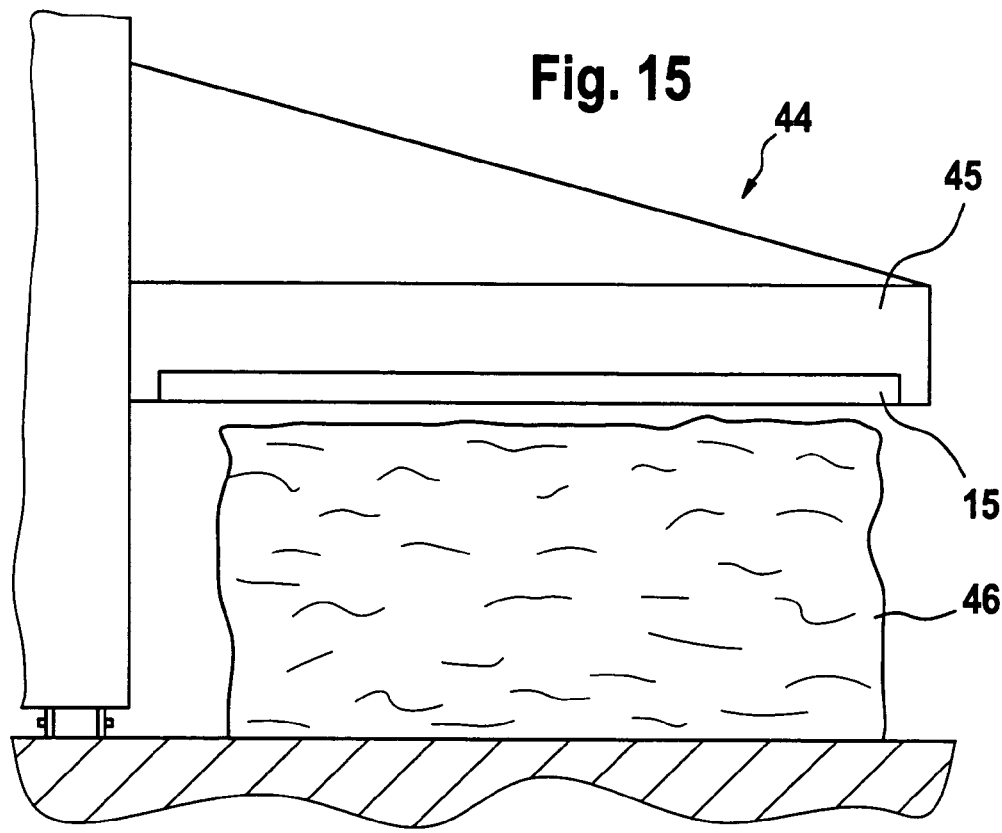
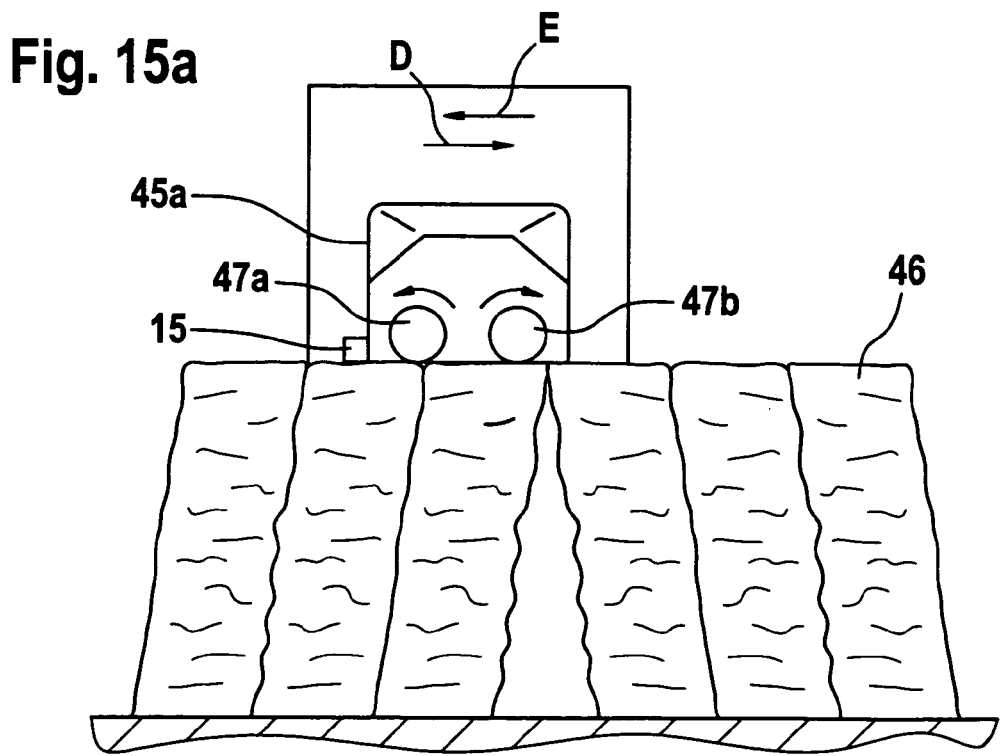

APPARATUS ON A TEXTILE FIBRE PROCESSING MACHINE FOR EVALUATING TEXTILE FIBRE MATERIAL

CROSS REFERENCE TO RELATED APPLICATION

This application claims priority from German Patent Application No. 102 33 011.5, which is incorporated herein by reference.

BACKGROUND OF THE INVENTION

The invention relates to an apparatus on a textile machine, such as a carding machine, wool carding machine, cleaning machine or the like for recording and evaluating textile fibre material.

In a known arrangement, across the width of a textile machine there is provided a fixed opto-electronic system, for example, a camera, which scans the moving fibre material and converts the measured values into electrical signals, the system being in communication with an image-evaluating device (with computer) which evaluates the raw data of the camera.

In the case of one known apparatus (DE 36 44 535), a conveyor belt is provided, along which a layer of fibre tufts moves relative to an image-recording apparatus, for example, a television camera. In this process, an approximately square zone is observed from above by means of the camera, which takes very short-exposure images and stores them in an image bank. The sequence of images corresponds to the belt speed, in that after forward feed of a measuring zone and re-starting of an entirely new zone, the next image is produced. The camera is arranged a substantial distance from the fibre tuft layer so that at least the width of the fibre tuft layer can be recorded. The use of an individual camera, which scans the fibre material across the entire width, disadvantageously necessitates considerable installation space, particularly in respect of height, which is needed owing to the physical optical path, especially the angle, of the camera objective.

It is an aim of the invention to produce an apparatus of the kind described in the introduction that avoids or mitigates the said disadvantages, which is especially simple and space-saving and permits a lower overall height combined with at least the same image quality.

SUMMARY OF THE INVENTION

The invention provides an apparatus on a textile fibre processing machine for inspecting and evaluating textile fibre material, the apparatus comprising an opto-electronic system for scanning the textile fibre material, there being relative movement between the opto-electronic device and the fibre material in a working direction and the fibre material having a working width extending transversely to said working direction, the opto-electronic system comprising two or more imaging devices which are displaced from one another across the working width of the fibre material and being in communication with a common image-evaluating device.

The use of a plurality of cameras, especially small camera modules, advantageously ensures that the entire region of the fibre sliver, especially a fibre fleece, to be inspected, is monitored simultaneously and moreover that the required overall space in respect of structural height is as small as possible. At the same time, the image quality remains at least the same or is even improved by the reduced distance.

The textile fibre material may be a fibre combination. The textile fibre material may be a fibre fleece. The textile fibre material may comprise fibre tufts. The textile fibre material may be a fibre web. The textile fibre material may be a fleece of fibre tufts. The textile material may be a fleece of fibre tufts. The textile material may be fibre waste.

The textile machine is advantageously a carding machine, a wool carding machine or a cleaning machine. In one advantageous arrangement, a fibre fleece is monitored at the output of a carding machine. In another advantageous arrangement, a fibre fleece is monitored at the output of a wood carding machine. Advantageously, the speed of the fleece is at least 40 m/min. Where a fibre sliver is inspected, that fibre sliver is located on a high-speed roller, for example, with clothing, needles, pins or the like. The high-speed roller may be arranged in an opener, cleaner, a carding machine, wool carding machine or the like.

Advantageously, the quality of the fibre combination, especially the fibre fleece, is assessed. Advantageously, foreign objects, e.g. trash, metal or the like in the fibre combination are detected. Advantageously, foreign fibres in the fibre combination are detected. Advantageously, the neps in the fibre combination, especially in the fibre fleece, are detected. Advantageously, each camera monitors a limited region (sub-region) of the fibre combination. Advantageously, the monitoring regions of adjacent cameras have a certain overlap. Advantageously, each camera comprises essentially an objective or the like and an image-recognition chip (sensor).

Advantageously, the camera is an electronic camera module. Advantageously, the camera module comprises at least one illuminating unit. Advantageously, the camera is a matrix camera. Advantageously, the camera is a line-scan camera (CCD camera). Advantageously, the monitoring regions border on each other without discontinuities. Advantageously, the entire width region of the fibre combination, especially of the fibre fleece, is monitored at once. Advantageously, the distance between objective and fibre combination allows a low overall height. Advantageously, the cameras are connected to a central evaluating device. Advantageously, at least the devices illuminating means, printed circuit board, synchronizer, power supply and/or device for reading out the individual pixels are provided centrally and singly for all camera modules. Advantageously, the camera modules are connected to a central evaluating device for processing the image information. Advantageously, evaluating devices are provided between a central camera-signal evaluation and the individual or grouped camera modules. Advantageously, the image evaluation device co-operates with an electronic control and regulating device, e.g. a microcomputer. Advantageously, the fibre combination is continuously moved. Advantageously, the cameras are arranged column-wise and side by side. Advantageously, the cameras—viewed in the direction of movement of the fibre combination—are arranged offset with respect to one another. Advantageously, there is provision for monitoring or checking of the fibre combination located inside the textile machine, e.g. carding machine, wool carding machine, cleaner or the like. Advantageously, there is provision for monitoring or checking of a fibre combination entering into or emerging from a textile machine. Advantageously, a display and/or shut-off device is arranged to be activated when foreign objects and/or foreign fibres are detected. Advantageously, the shut-off device co-operates with an evaluating device for the size and/or type of foreign object and/or foreign fibre. Advantageously the shut-off device is associated with a set value generator. Advantageously the fibre orientation in the incoming and/or out-going fibre combination, especially fibre fleece, is detectable. Advantageously, the uniformity (cloudiness, distribution between fibres and voids) of the fibre combination, especially fibre fleece, is detectable. Advantageously, holes in the fibre fleece are detectable. Advantageously, the fleece form in the marginal zones is detectable. Advantageously, the fibre material located on the cylinder of a carding machine is detectable. Advantageously, in the case of a cleaning machine, there is provision for the degree of contamination of the in-coming and/or out-going fibre material to be monitored. Advantageously, the efficiency and/or the cleaning performance of the cleaner is determinable from the measured results of the contamination degree of the in-coming and/or out-going fibre material. Advantageously, the efficiency and/or cleaning performance is used to adjust working elements of the cleaner and/or of upstream and/or downstream machines. Advantageously, there is provision for assessment of the waste of the textile machine. Advantageously, the waste flow is guided past, for example transported past, the camera modules, or sensors. Advantageously, the camera modules are mounted at the waste discharge devices, for example, suction hoods, for continuous monitoring of the waste. Advantageously, the camera modules are used for detection of foreign objects and/or foreign fibres with subsequent removal thereof from the system, for example, by blowing out. Advantageously, the removal from the system is effected as a function of the position of at least one detecting camera module. Advantageously, the removal from the system of the foreign objects and/or foreign fibres is effected selectively.

The invention also provides an apparatus for inspecting and evaluating a fibre material found in textile technology, for example, fibre bales, tufts, fleece or the like, in which moving sensors scan the stationary fibre material and the measured values are converted into electrical signals, the sensors being in communication with an image-evaluating device (with computer), which evaluates the raw data of the cameras, characterized in that three or more opto-electronic sensors, for example, cameras, are provided side by side and, in relation to the unit of width, the number of cameras increases as the distance between the objective and fibre combination decreases.

The textile machine may be a bale opener. Advantageously, the sensors are arranged on or in the movable stripping head of the bale opener. Advantageously, the sensors scan the bale surface. Advantageously, the sensors are movable in the lengthwise direction of the fibre material, for example, a row of fibre bales. Advantageously, the degree of cleaning of the fibre material is determinable by a comparison of the measured results of at least two successively arranged apparatuses each having a plurality of cameras. Advantageously the efficiency of the machine is determinable by a comparison of the measured results of at least two successively arranged apparatuses each having a plurality of cameras. Advantageously, the degree of cleaning and/or the efficiency of an installation comprising several machines is determinable by a comparison of the measured results of at least two successively arranged apparatuses and a respective plurality of cameras. Advantageously, the installation comprises a plurality of blowing room machines. Advantageously, the installation comprises a plurality of carding machines. Advantageously, the number of sub-regions increases as the distance between the cameras and the fibre material decreases. Advantageously, the measurements are effected on line.

The invention also provides an apparatus on a spinning machine, such as a carding machine, wool carding machine, cleaning machine or the like for evaluating textile fibre material, in which across the width of a textile machine a fixed opto-electronic system, for example, a camera, is provided, which scans the moving fibre material and converts the measured values into electronic signals, the system being in communication with an image-evaluating device (with computer) which evaluates the raw data of the camera, characterized in that two or more cameras are provided side by side and, in relation to the width, the number of cameras increases as distance between the image-recognition unit and textile fibre material decreases.

According to a preferred embodiment, the cameras are camera modules, which preferably comprise only the most essential components, especially the objective and image-recognition chip. All other functions going beyond image capture and acquisition are preferably taken care of by a respective common device for at least two camera modules. Instead, a central device for all camera modules can be provided. Any increased outlay compared with the known arrangement, owing to the use three or more cameras, is advantageously offset in accordance with the invention at least by the use of inexpensive camera modules combined with few devices or just one central unit. In addition, a structurally simple apparatus is thereby achieved.

Furthermore, the invention provides a method of monitoring and evaluating textile fibre material, comprising effecting relative movement between the fibre material and an opto-electronic monitoring device comprising a plurality of opto-electronic sensor devices in a working direction, monitoring a respective monitoring region by means of each opto-electronic sensor device, the monitoring regions being laterally displaced from one another across a working width of the fibre material, and evaluating data from the sensor devices.

BRIEF DESCRIPTION OF THE DRAWINGS

FIG. 10a is a plan view of a pneumatic foreign object separation device;

FIG. 15 is a schematic front view of a bale opener with the apparatus according to the invention;

FIG. 15a is a side view of the bale opener of FIG. 15 with a first embodiment of an apparatus according to the invention;

DESCRIPTION OF THE PREFERRED EMBODIMENTS

Figure 1:
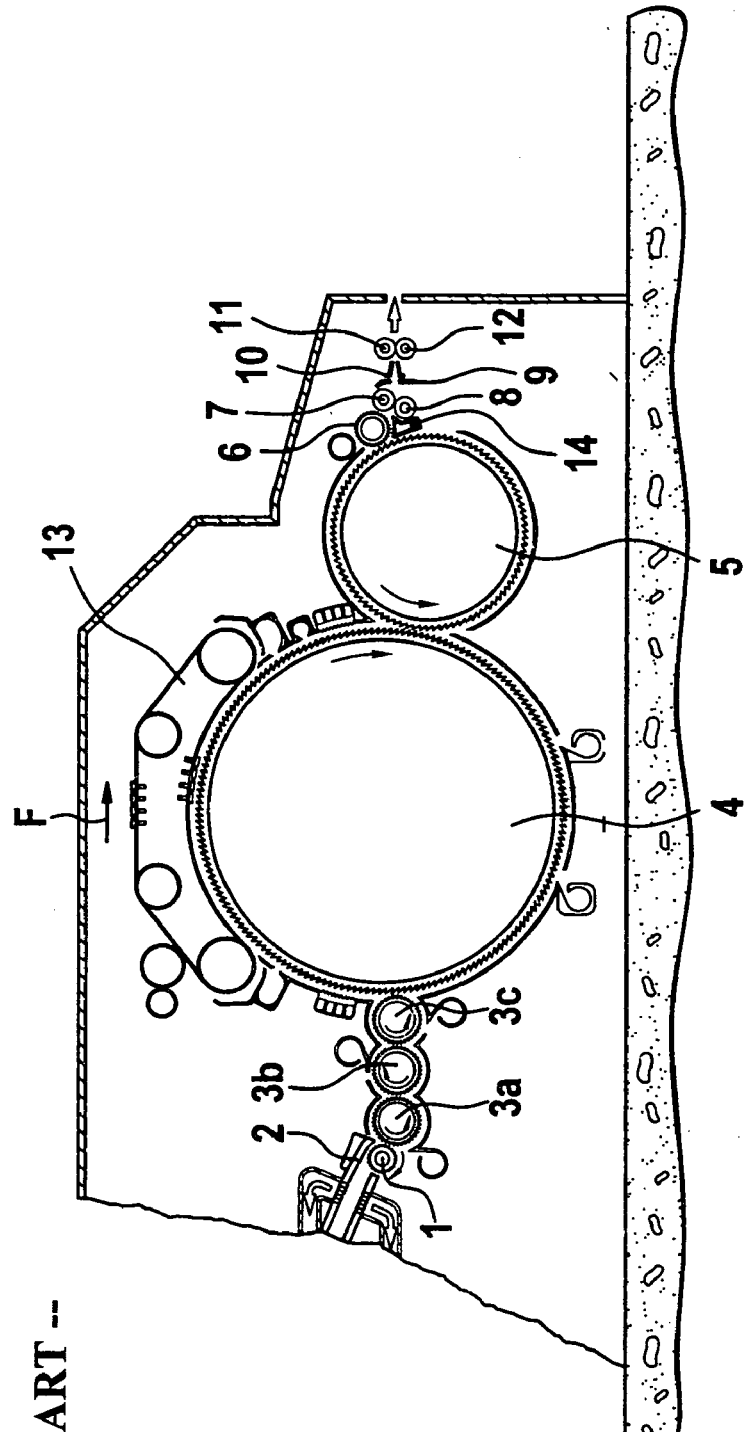
FIG. 1 is a schematic side view of a carding machine with a supporting and guiding member for receiving a camera according to the invention and the illuminating devices.

With reference to FIG. 1 shows a carding machine, for example, a high performance card DK 903 (trade mark—manufactured by Trützschler GmbH & Co KG of Mönchengladbach, Germany), with feed roller 1, feed table 2, licker-ins 3a, 3b, 3c, cylinder 4, doffer 5, stripping roller 6, squeezing rollers 7, 8, web-guide element 9, web funnel 10, take-off rollers 11, 12 and revolving card top 13. Beneath the stripping roller 6 there is a stationary supporting and guiding member 14. The upper squeezing roller is arranged in close proximity to the stripping roller 6. The directions of rotation of the cylinder and the rollers are shown by respective curved arrows. The supporting and guiding member 14 serves to accommodate an apparatus 15 according to the invention. The letter F denotes the working direction.

Figure 2:
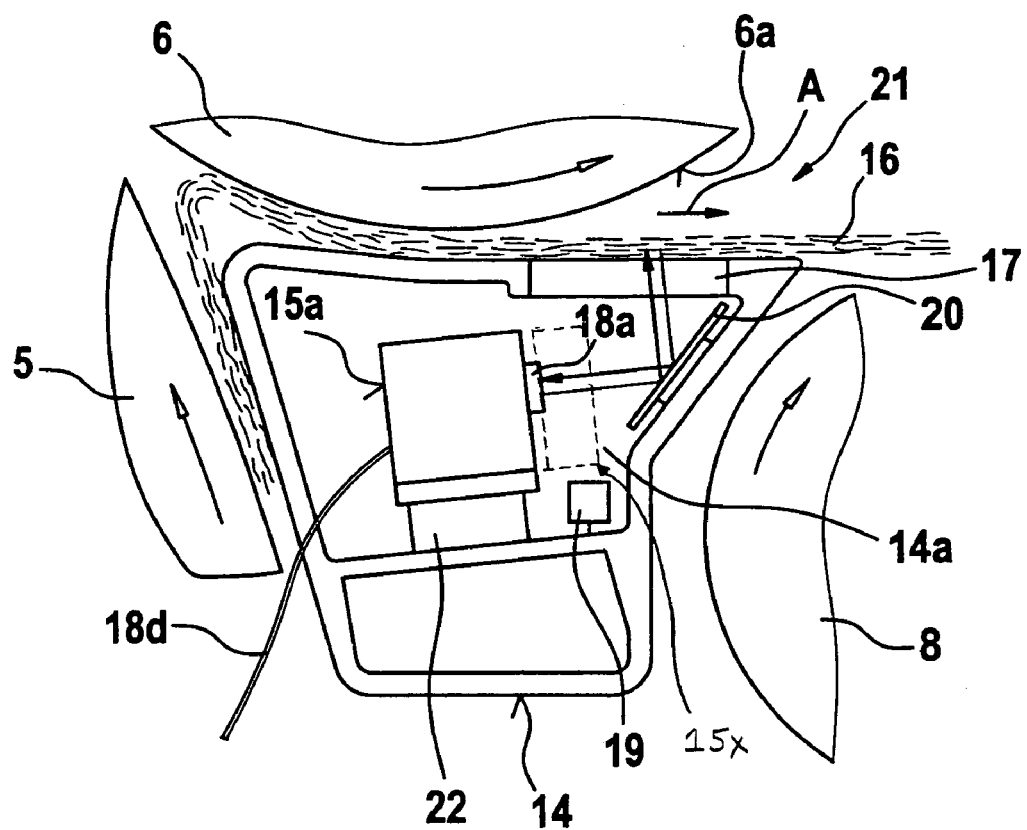
FIG. 2 is a side view of an apparatus according to the invention on the carding machine according to FIG. 1 with the fibre web to be filmed.

In FIG. 2, the reference number 21 denotes the region in which the removed fibrous web 16 passes from the stripping roller 6 to the squeezing rollers 7, 8. The supporting and guiding member 14 has essentially a four-cornered cross-section. The upper surface of the member 14 is slightly concavely curved. The radius of curvature of the curve of the upper surface is greater than the radius of curvature of the stripping roller 6. The arrow A indicates the running direction of the fibrous web 16. The element 14 is in the form of a housing, a transparent window 17 being provided in the sliding contact region. The fibrous web 16 is located initially on the clothing of the doffer 5, is guided in the roller nip between doffer 5 and stripping roller 6 around and over the clothing 6a of the stripping roller 6, is detached from the stripping roller 6 a little way after the region of the perpendicular diameter, is guided in the region of the window 17 in direction A, following the end region runs completely freely and finally enters the roller nip between the squeezing rollers 7, 8 and passes between these. The upper surface of the element 14 faces towards the clothing 6a of the stripping roller 6. With its one end region, the element 14 is associated with the roller nip between doffer 5 and stripping roller 6. The other end region is arranged in the region between stripping roller 6 and squeezing rollers 7, 8, the edge thereof being aligned in the direction towards the roller nip between the squeezing rollers 7, 8. The element 14 is an extruded profile, for example, of aluminium, with an inner cavity (14a). Fixed cameras 15a to 15n (see FIG. 3), for example, diode matrix cameras, an illuminating device 19 (see FIG. 4), for example, comprising several light-emitting diodes 19a to 19n, and a reflecting mirror 20 are arranged in the interior 14a of the housing 14. The reflecting mirror 20 is arranged at an angle between the objective 18a of the cameras 15a to 15n and the illuminating device 19 on the one hand and the inside of the window 17 on the other hand. The fibrous web 16 runs over the outside of the window 17 in direction A. The window 17, for example of glass, is kept clean by contact with the moving fibre material. The cameras 15a to 15n (only camera 15a is shown in FIG. 2) are arranged on a common support 22, which is secured to the element 14. Reference numeral 18d indicates a communication cable.

Figure 3:
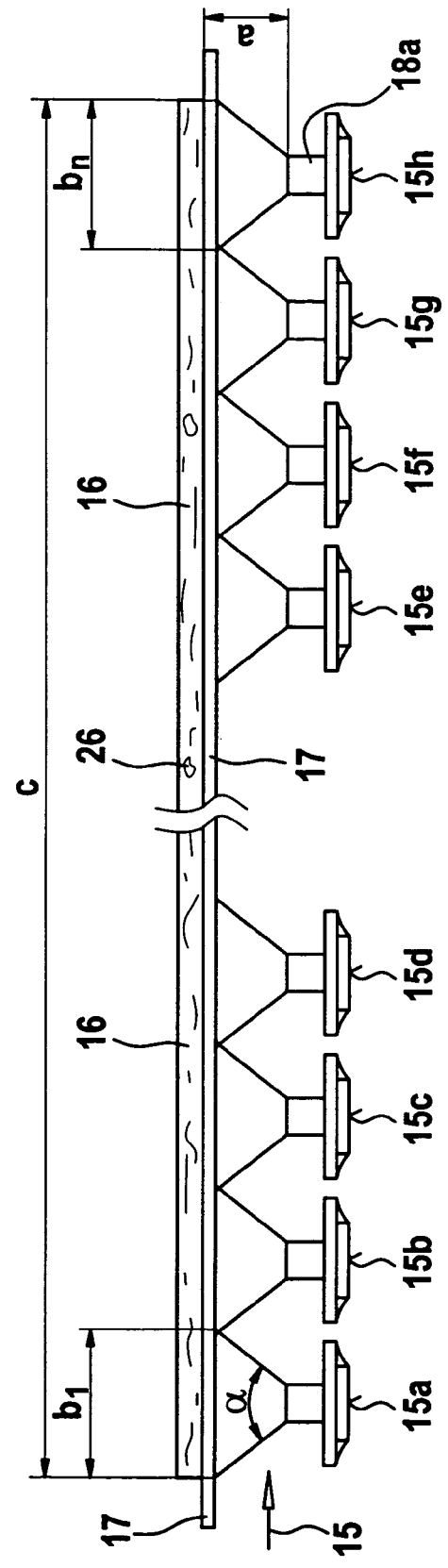
FIG. 3 is a front view of a plurality of cameras arranged side by side across the width of a machine.

FIG. 3 shows the plurality of camera modules 15a to 15n arranged side by side across the width c of a machine, for example that of FIG. 1. The distance a of the objective 18a from the fibre material 16 is small. Each camera module 15a to 15n monitors or detects a sub-region $b_1$, $b_2$ to $b_n$ of the total width c of the fibre material 16 (card web). The monitoring regions $b_1$ to $b_n$ (sub-regions) of the adjacent camera modules 15a to 15n have a certain overlap. The reference number 26 denotes the impurities to be detected, e.g. trash and the like. When the distance a between the objectives 18a of the camera modules 15a to 15n and the fibrous web 16 is selected to be smaller (in a manner not shown), for example, to save space in construction, the number of camera modules 15a to 15n—in relation to a constant width c of the textile machine or of the fibrous web 16 to be detected—increases. If the optical path, that is, the image angle α, remains the same, the number of detected sub-regions $b_1$ to $b_n$ increases. The image angle α for recording a relatively large sub-region $b_1$ to $b_n$ is thereby prevented from enlarging with a decreasing distance a and hence impairing the image quality. The camera modules can also be offset with respect to one another alone the running direction A. For example, a camera module 15x (shown schematically and in dashed lines in FIG. 2) can be offset in the running direction A with respect to camera module 15a.

Figure 4:
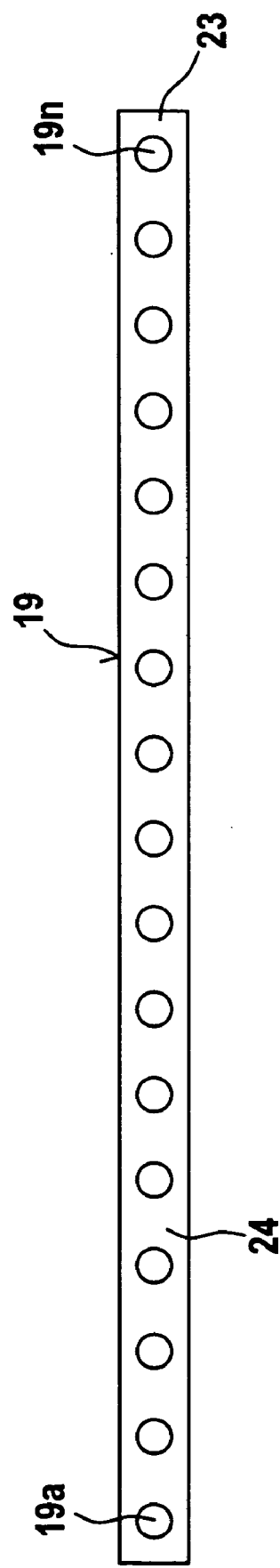
FIG. 4 is a front view of a plurality of illuminating devices arranged side by side across the width of a machine.

In the illuminating device 19 illustrated in FIG. 4, a plurality of light-emitting diodes 19a to 19n are arranged side by side on a common supporting element 23, 24.

Figure 5:
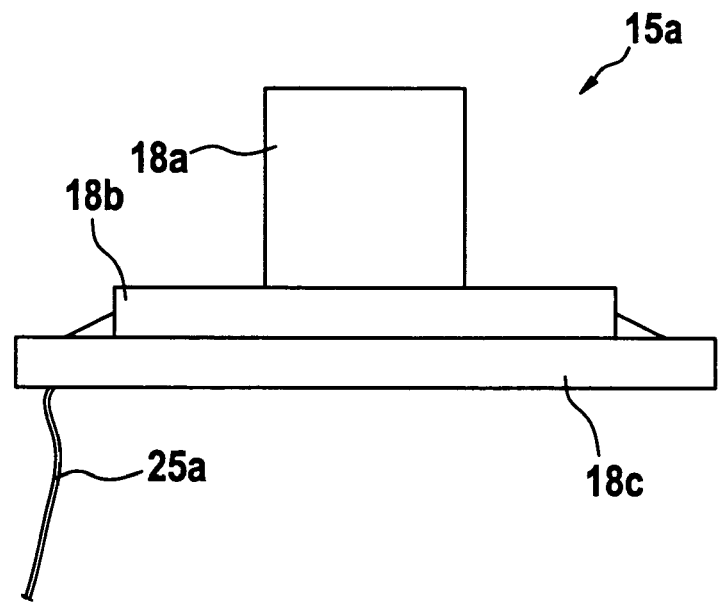
FIG. 5 is a front view of a camera module with objective, image-recognition chip and the like and guide plate.

With reference to FIG. 5, a camera module 15a suitable for use in the apparatus of FIGS. 2 to 4, is constructed so that an image-recognition chip 18b (sensor) is arranged between the objective 18a (which can alternatively be a lens or other component of identical function) and a printed circuit board 18c. The reference numeral 25a denotes an electrical lead. Alternatively, it is possible to use an image-recognition chip with which image recognition as such is possible, i.e. with no special objective, or with a component of identical function integrated in the chip.

Figure 6:
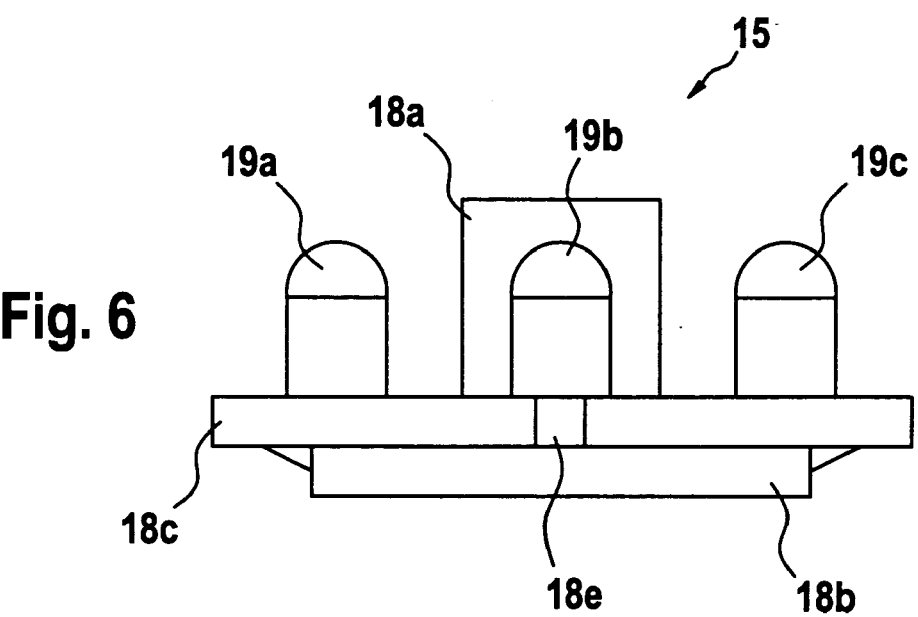
FIG. 6 is a front view of a camera module similar to that of FIG. 4, with the addition of illuminating devices.

In the embodiment of FIG. 6, a camera module 15' is constructed so that the printed circuit board 18c is provided between the objective 18a and the image-recognition chip 18b. In the printed circuit board 18c there is a continuous opening 18e, which allows the passage of optical rays. As well as the objective 18a, light-emitting diodes 19a, 19b and 19c are arranged on the printed circuit board 18c.

Figure 7:
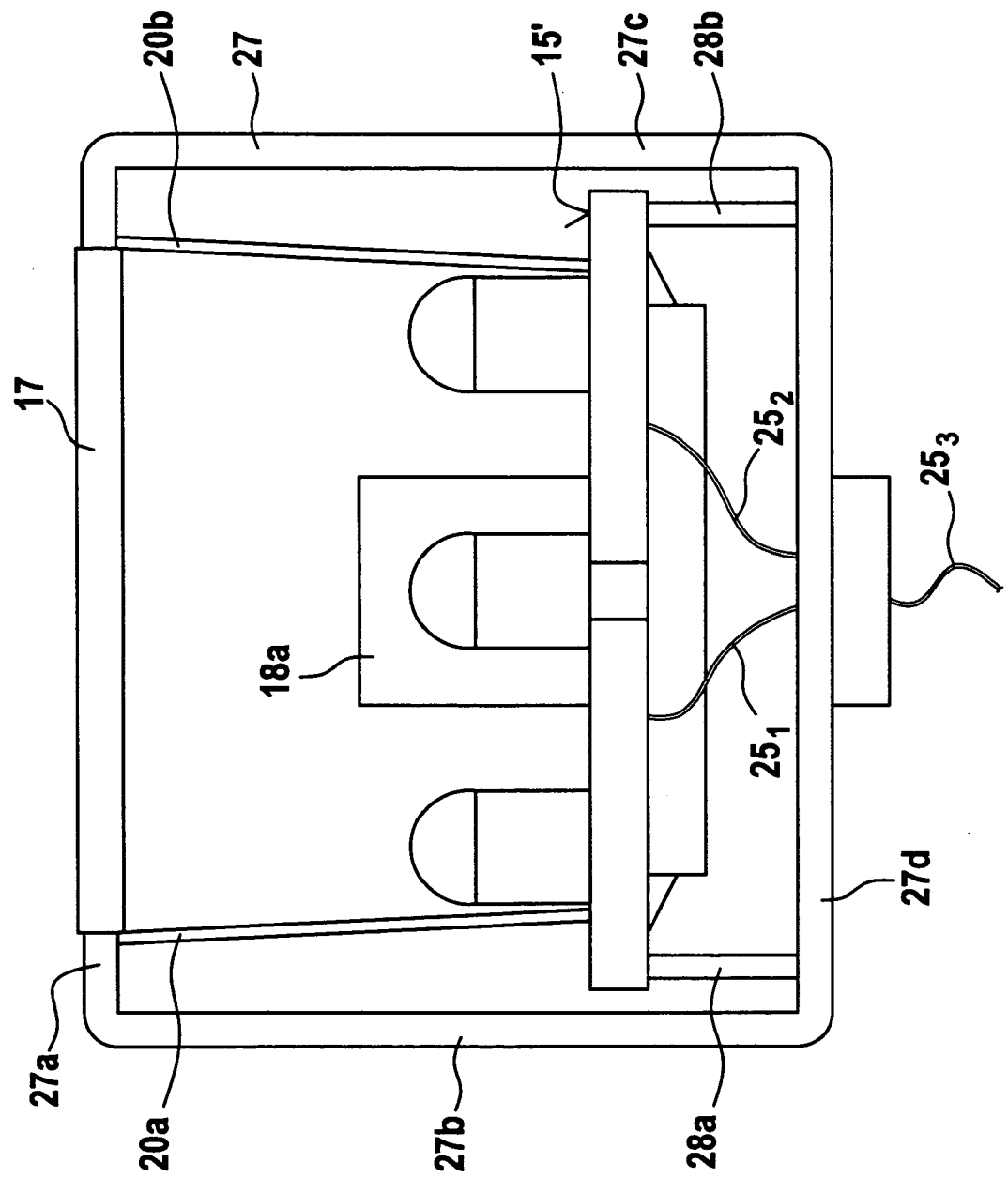
FIG. 7 is a section through a housing for a plurality of camera modules.

In the embodiment of FIG. 7, a plurality of camera modules 15' is arranged inside a housing 27. The transparent window 17 is provided in a top plate 27a of housing 27. Between the camera module 15' and the side walls 27b, 27c there are two mirrors 20a and 20b. Between the camera module 15' and the base plate 27d there are two spacers 28a and 28b. The electrical leads $25_1$, $25_2$ lead to an electrical connecting cable $25_3$. Each camera module 15' is as described with reference to FIG. 6.

Figure 8:
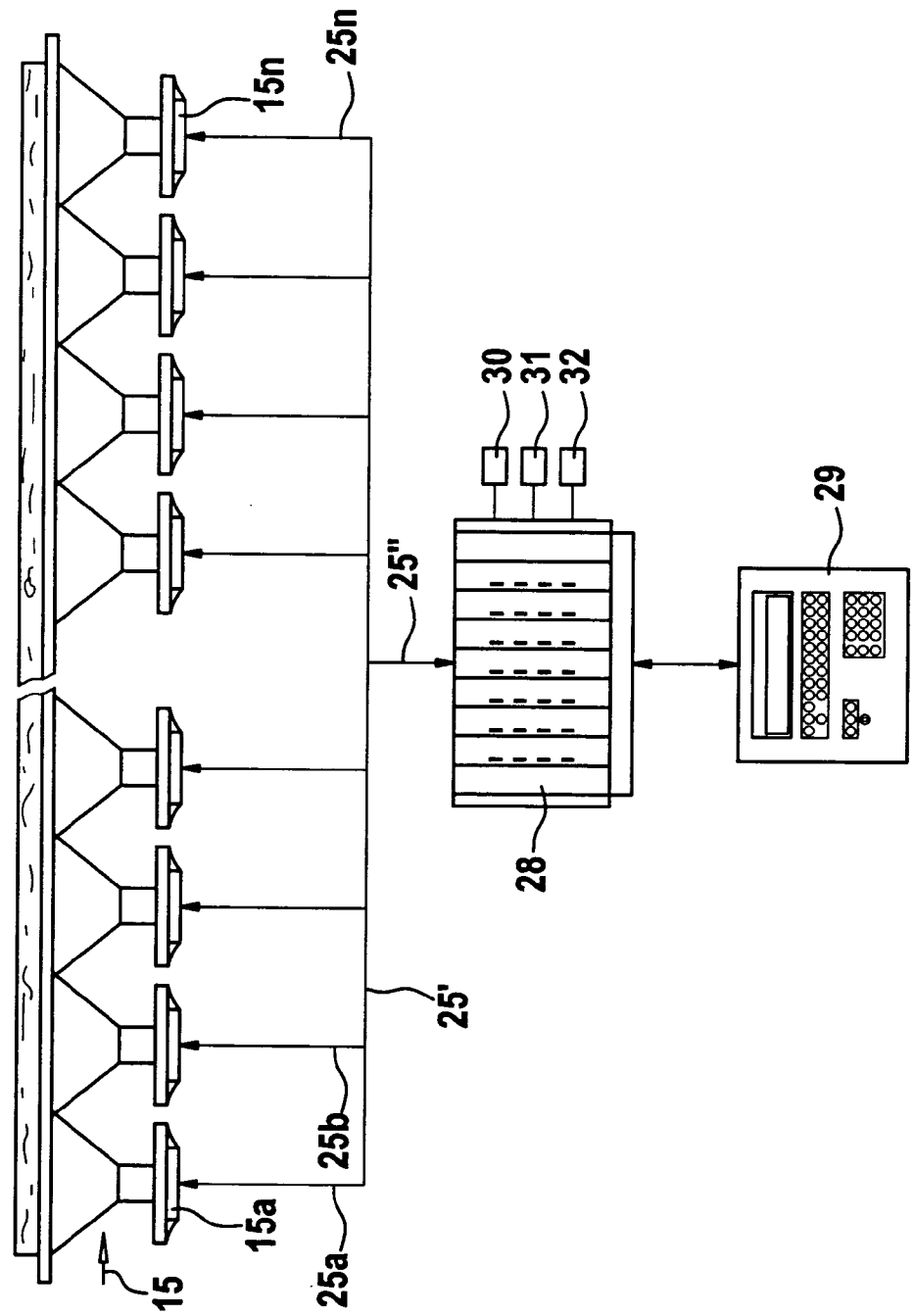
FIG. 8 is a front view of an embodiment having a plurality of camera modules with attached central control device and centralised image evaluation.

In the embodiment of FIG. 8, camera modules 15a to 15n are connected by way of electrical leads 25a to 25n, 25' and 25" to a central machine control system 28 (microcomputer control and regulating device), for example, TMS-2 (Trützschler Microcomputer Steuerung made by Trützschler GmbH & Co KG of Mönchengladbach, Germany). An operator unit 29 (keyboard and monitor), an image evaluation unit 30, a control unit 31 and a foreign object separation device 32 are also connected to the machine control 28.

The electronic image evaluation on the basis of the electrical signals supplied by the camera modules 15a to 15n can be effected, for example, in accordance with the manner described in DE-OS 199 43 079. The image evaluation can have several aims:

a) The textile fibre material can be assessed with regard to technological characteristics, for example, degree of contamination, number of neps, fibre distribution and the like. An individual apparatus 15 according to the invention can be employed for that purpose. When at least two series-connected apparatuses are used, the performance (efficiency) of the machine can be determined from a comparison of the analysed measured data. An appropriate display device 30, for example, a graphic display or the like, can be provided for the assessment.

b) At least one step can be taken to modify the technological characteristics of the fibre material, for example, the fibre web 16, by adjustment to elements of the machine. A control means 31, which acts on the machine, can initiate measures for changes in the fibre material 16, for example, it can change the spacing between the card top clothings and the cylinder clothing of the card, the speed of the cylinder 4, the spacing of a guide element from a roller, the sharpening of the roller clothings or the like.

c) Furthermore, at least one step can be taken to remove unwanted constituents, such as impurities, trash, neps and the like from the fibre material. For that purpose, a removal device 32 that acts on the fibre material is provided. This can be, for example, a pneumatic foreign object separating device 32, as shown in FIG. 10, 10a.

The aims a), b), c) can be individual aims, or they can be combined.

Figure 9:
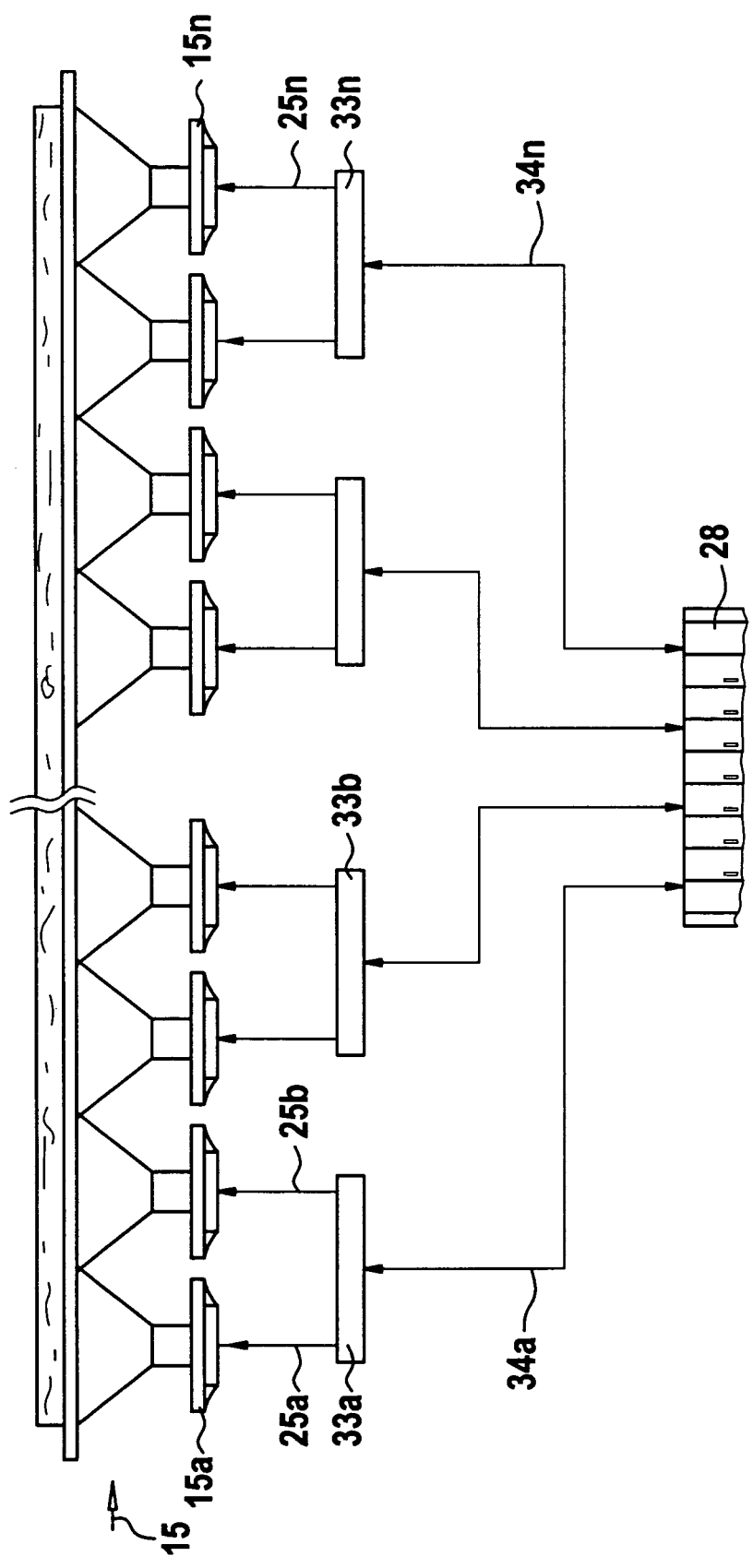
FIG. 9 is a front view of a further embodiment having a plurality of camera modules with attached central control system as in FIG. 8, but with decentralised image evaluation.

In the embodiment of FIG. 9, a decentralised evaluation of the raw data of the camera modules 15a to 15n is provided. For that purpose, a plurality of evaluating devices 33a to 33n is provided between the camera modules 15a to 15n and the machine control system 28, two camera modules 15a to 15n being connected to each evaluating device 33a to 33n via lines 25a to 25n. The evaluating devices 33a to 33n are connected to the machine control system 28 via lines 34a to 34n.

Figure 10:
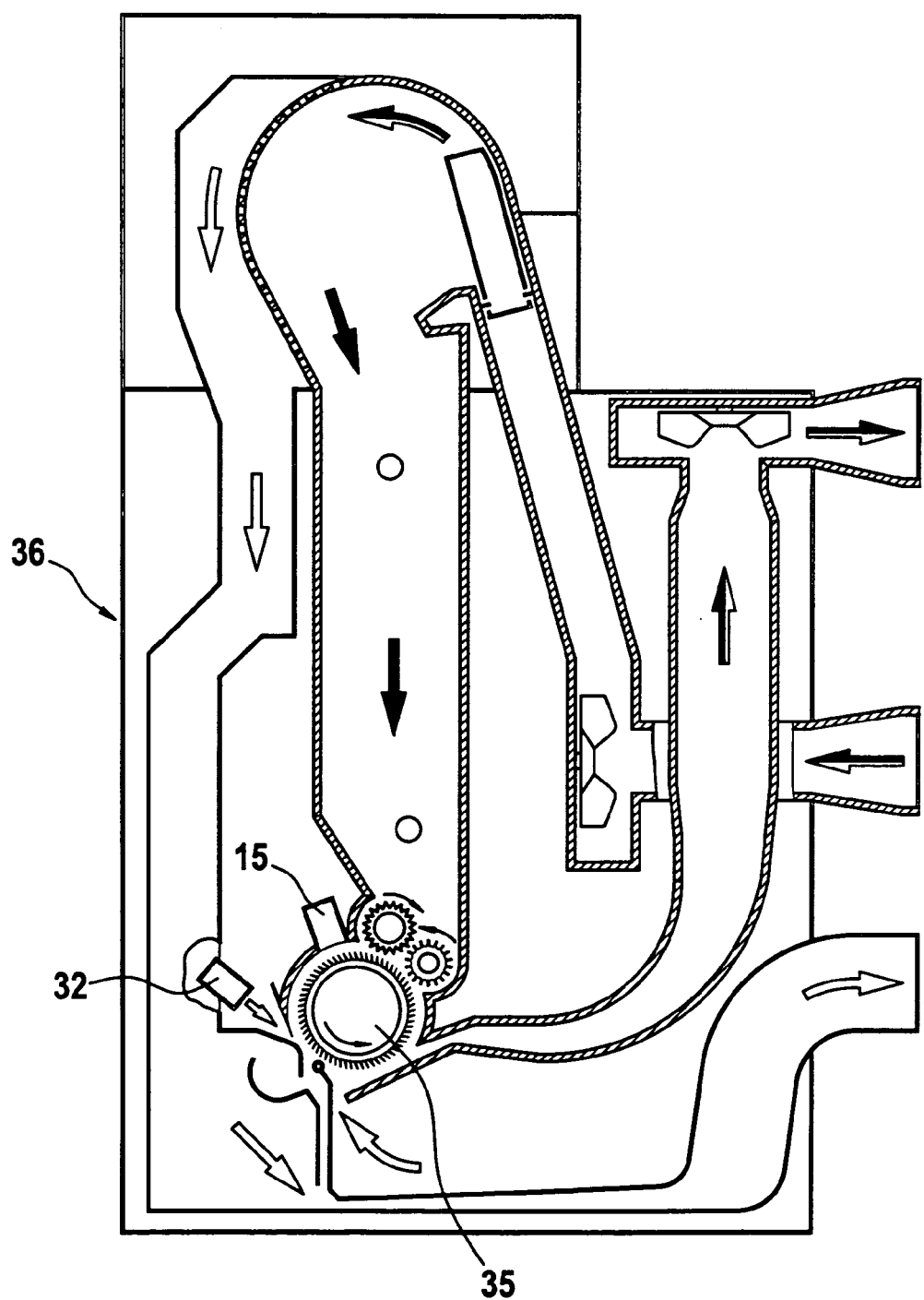
FIG. 10 is a side view of an apparatus according to the invention on a foreign object recognition and separation device having a high-speed roller.

In the embodiment of FIG. 10, an apparatus 15 according to the invention is associated with the high-speed roller 35 of a foreign object recognition and separation device 36, e.g. a SECUROMAT SCFO (made by Trützschler GmbH & Co KG of Mönchengladbach, Germany). Viewed in the direction of rotation of the roller 35, downstream of the device 36 there is arranged a pneumatic foreign object separating device 32, which, as shown in FIG. 10a, comprises a plurality of blast nozzles 32a to 32n across the width of the machine 36. The machine control system 28 (which may be analogous to that described with reference to FIGS. 8 and 9), to which the apparatus 15 according to the invention and the device 32 are connected, always functions in response only to one nozzle 32a to 32n or to two adjacent nozzles 32a to 32n, in the operative region of which the foreign object 26 has been detected. As a consequence, only a few fibre tufts (only 1–2 g) of cotton per separation process are removed. This permits a selective, sensitive adjustment of the system to enable even small parts 26 to be separated out without allowing an unduly high loss of fibre material.

Figure 11:
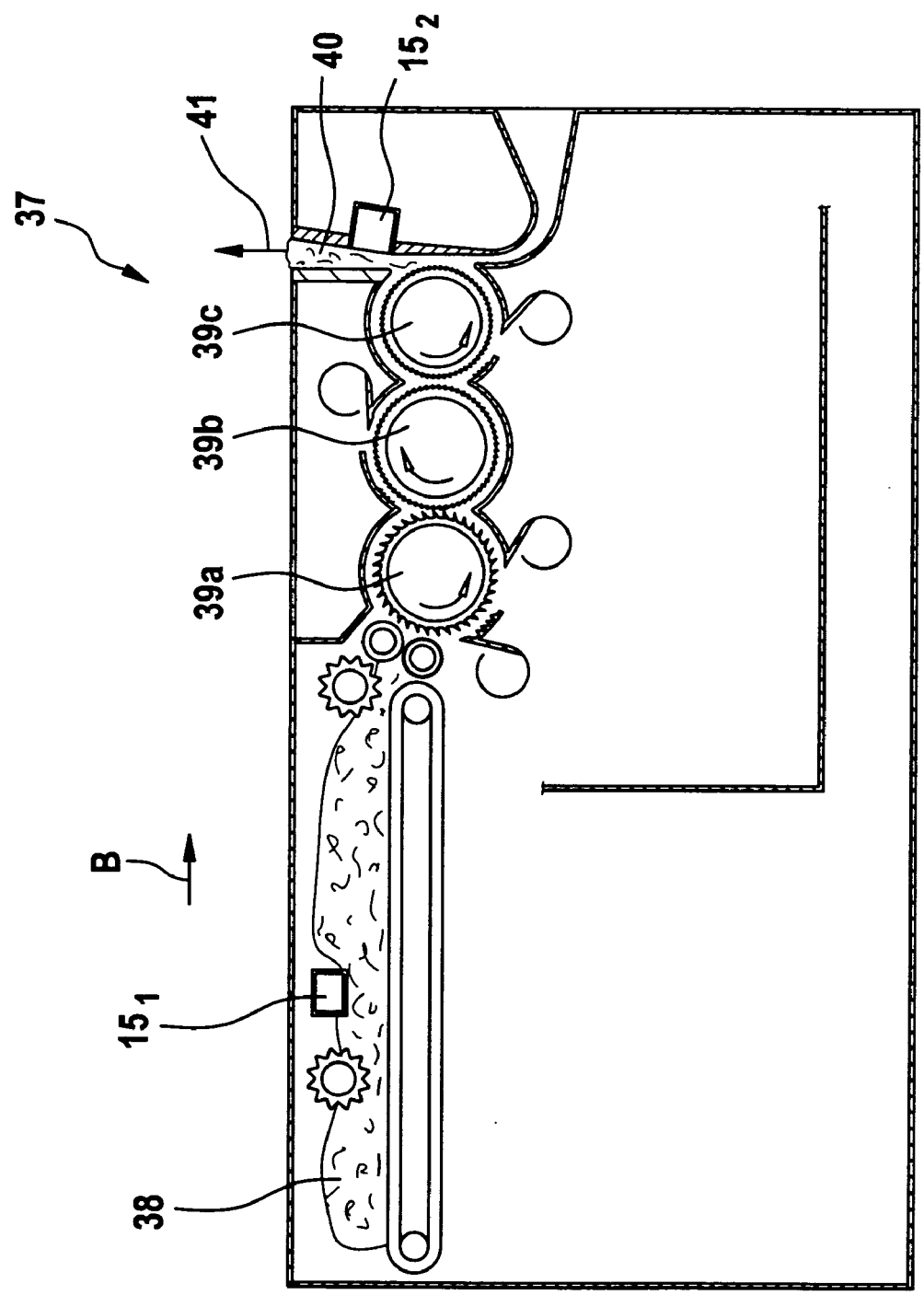
FIG. 11 is a side view of a cleaner having two apparatuses according to the invention, one associated with the incoming fibre material and one with the removed fibre material.

In the embodiment of FIG. 11, two apparatuses $15_1$ and $15_2$ according to the invention are mounted on a cleaning machine 37, e.g. a CLEANOMAT VCT 3 (made by Trützschler GmbH & Co KG of Mönchengladbach, Germany). The one apparatus $15_1$ is associated with the fibre tuft material 38, e.g. cotton, entering the cleaning machine 37, and the other apparatus $15_2$ is associated with the fibre tuft material 41 (arrow) removed by the last roller 39c —viewed in the working direction B—of the multiple roller cleaner 37 and discharged through a pipeline 40. The apparatuses $15_1$ and $15_2$ are connected to the machine control system 28 (FIGS. 8, 9), and by a comparison on the basis of the image evaluations enable the cleaning performance of the cleaner 37 to be determined.

Figure 12:
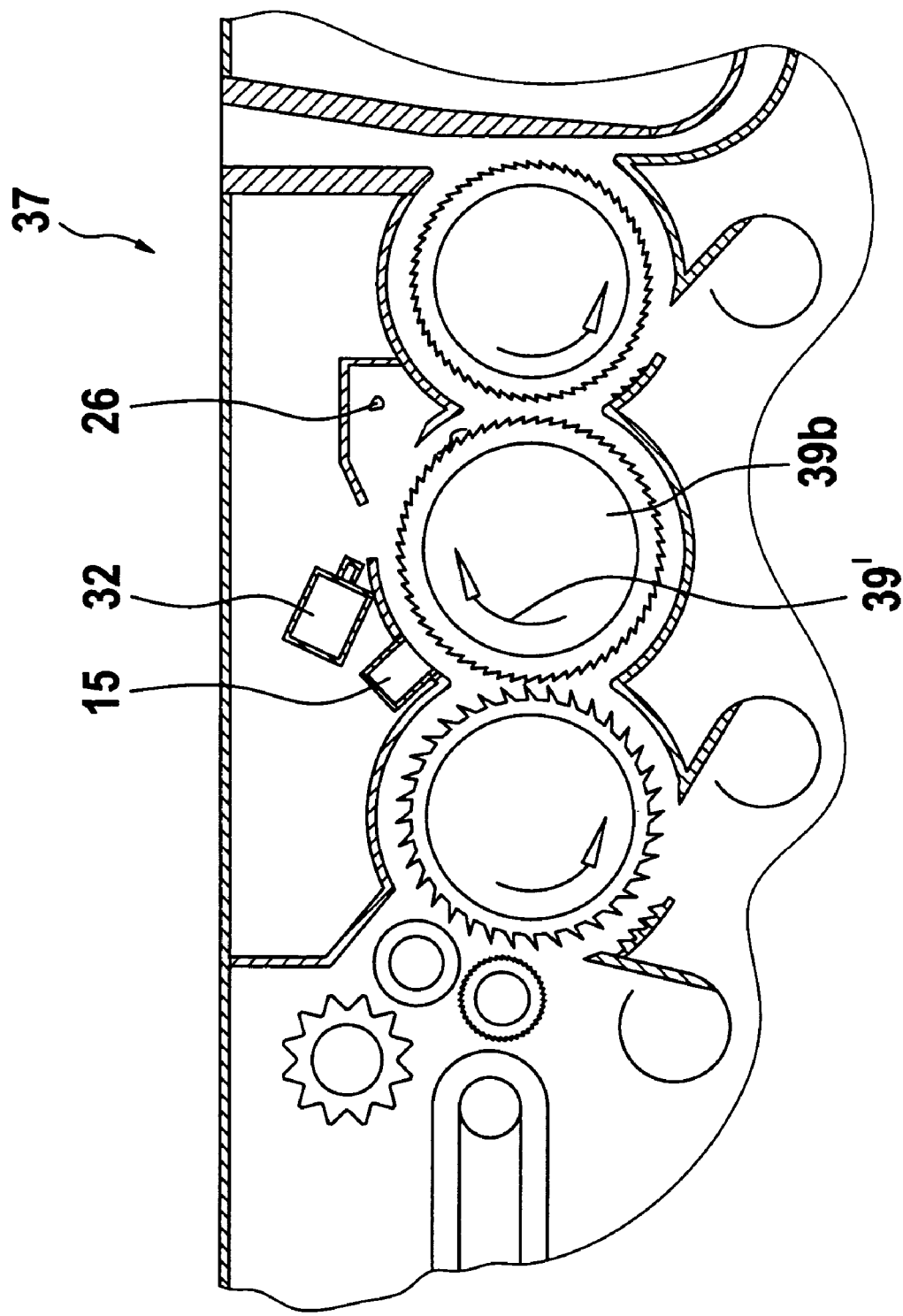
FIG. 12 is a side view of an apparatus according to the invention associated with a high-speed roller of a cleaner with a pneumatic foreign object separation device.

In the embodiment of FIG. 12, an apparatus 15 according to the invention and a pneumatic foreign object separation device 32, for example of the construction shown in FIGS. 10, 10a, are associated with the middle roller 39b of a cleaner 37, viewed in the direction of rotation 39' of the roller 39b.

Figure 13:
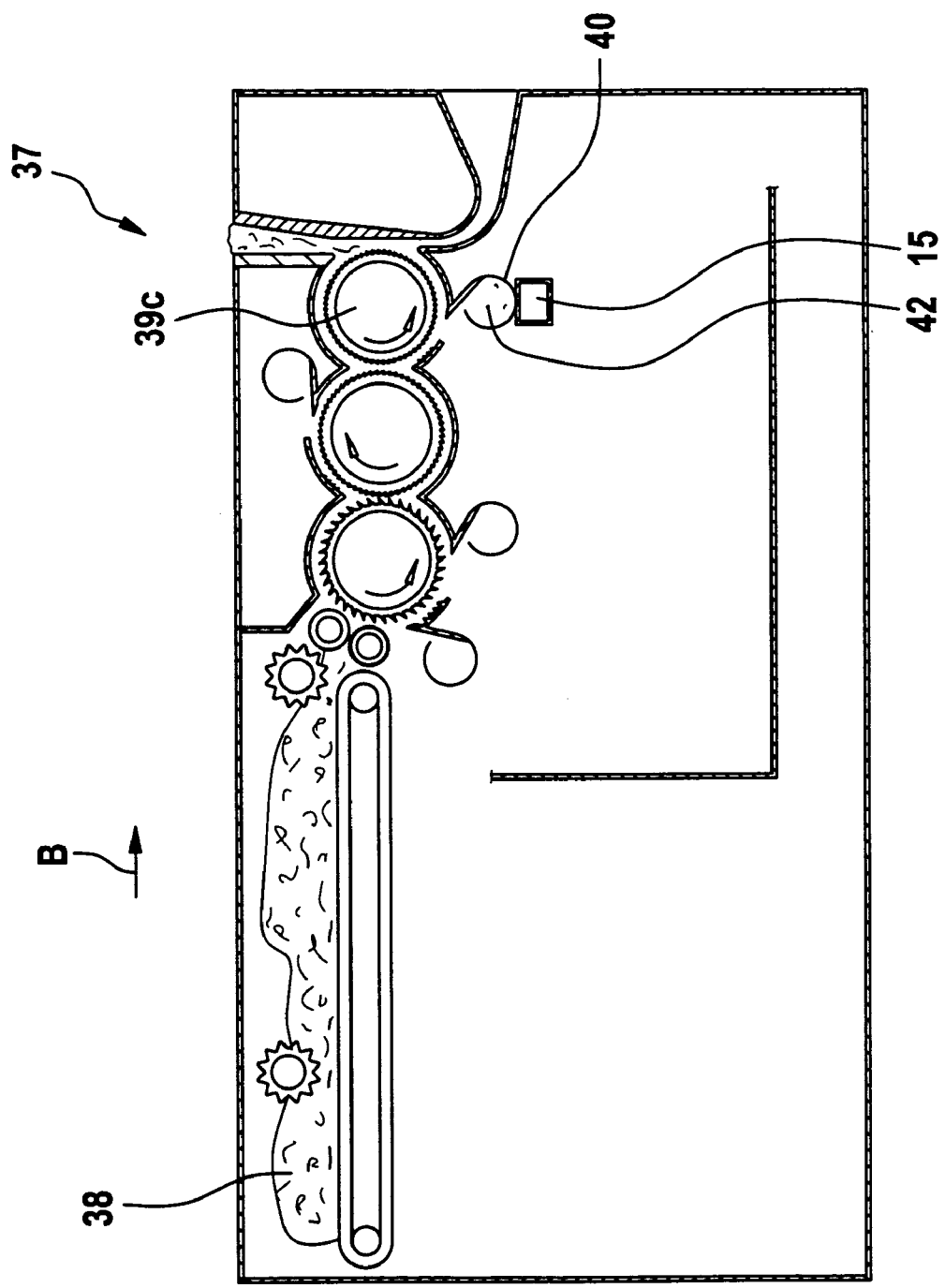
FIG. 13 is a side view of an apparatus according to the invention associated with a waste-collecting device on a cleaner.

In the embodiment of FIG. 13, a separating blade, a separating opening and a suction hood 40 are arranged beneath the roller 39c of the cleaner 37. The impurities 42 separated from the fibre material 38 are collected in the suction hood 40 and extracted pneumatically. A small proportion of fibre is separated with the impurities 42. An apparatus 15 according to the invention, which detects the separated impurities 26, including the small proportion of fibre, is associated with the suction hood 40. The apparatus 15 is connected to the machine control system 28 (which may, for example, be analogous to that of FIGS. 8, 9).

Figure 14:
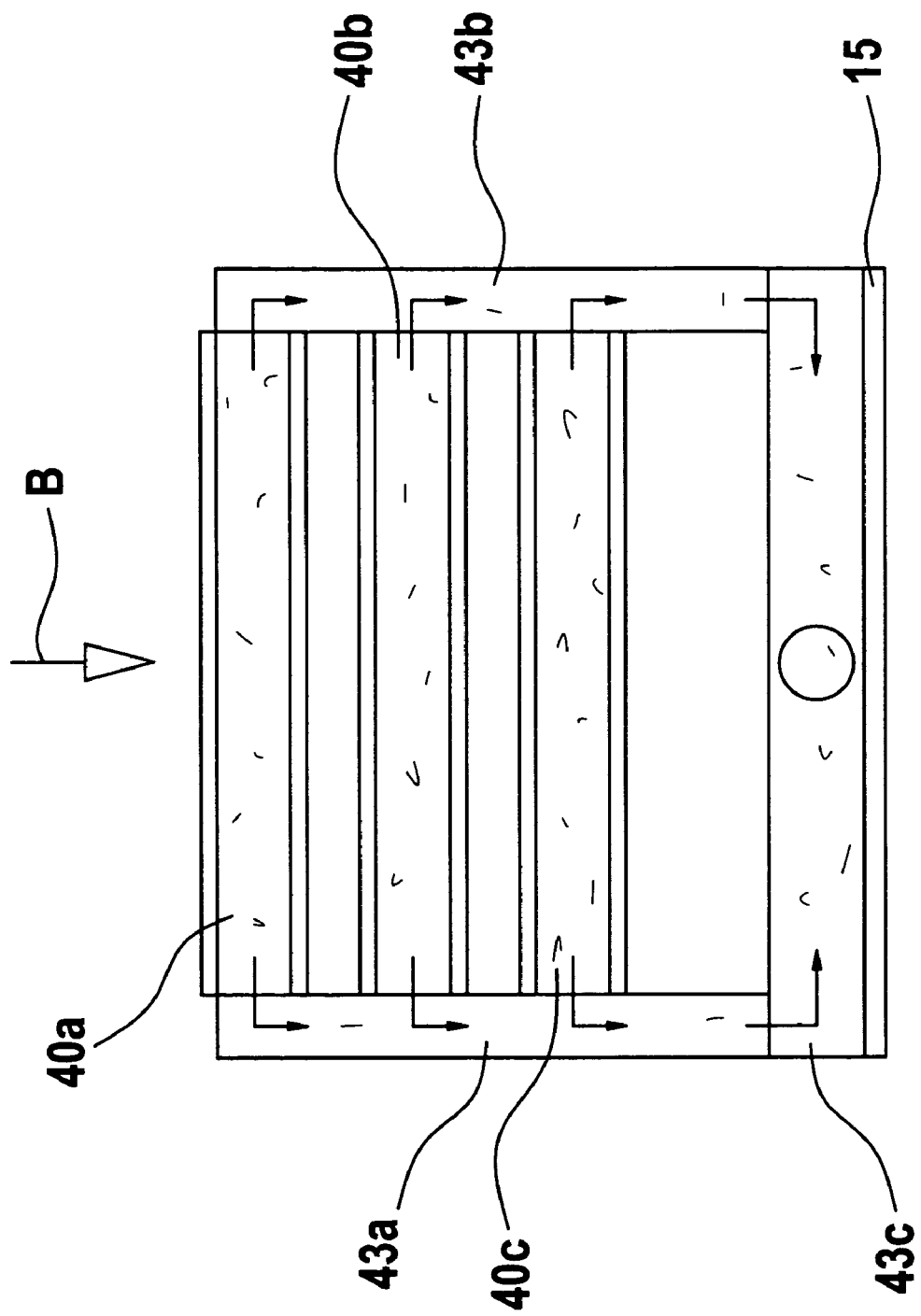
FIG. 14 is a schematic plan view of an apparatus similar to that of FIG. 13, but with a central waste-collecting device.

As shown schematically in FIG. 14, suction hoods 40a, 40b and 40c are connected by way of suction lines 43a, 43b (lateral waste collectors) to a central waste extraction line 43c, with which an apparatus 15 according to the invention is associated. The reference letter B denotes the flow of fibre material through the machine.

Figure 15B:
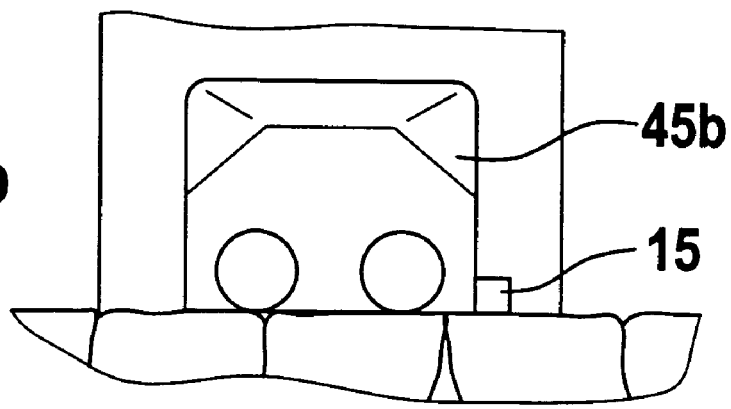
FIG. 15b is a side view of the boom shown in FIG. 15 with a second embodiment of the apparatus according to the invention.
Figure 15C:
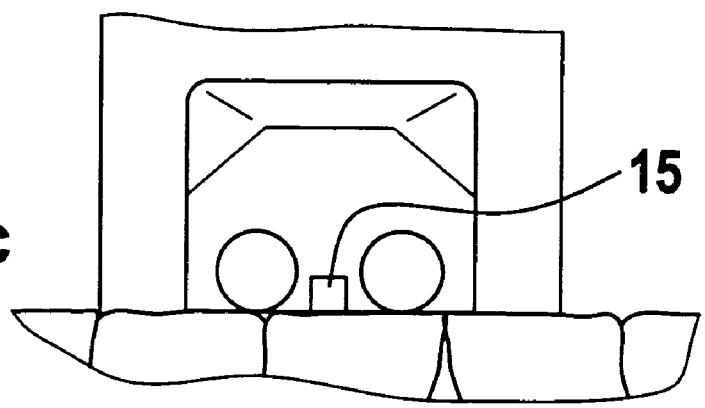
FIG. 15c is a side view of the boom shown in FIG. 15 with a third embodiment of the apparatus according to the invention.

In the embodiment of FIG. 15, an apparatus 15 according to the invention is mounted on the travelling boom 45 on an automatic bale opener 44, e.g. a BLENDOMAT BDT (by Trützschler GmbH & Co KG of Mönchengladbach, Germany). As shown in FIG. 15a, the boom 45 travels back and forth in the direction of arrows D and E above a row of stationary fibre bales 46. Within the boom 45 there are two high-speed stripping rollers 47a, 47b, which remove fibre tufts from the surface of the fibre bales 46, the tufts being sucked off pneumatically. The apparatus 15 is mounted at the lower end of a lateral wall 45a of the boom 45. The fibre material, especially cotton, of the fibre bales 46 is detected by the apparatus 15. In another embodiment of FIG. 15b, the apparatus 15 is secured to the other lateral wall 45b of the boom 45. In accordance with yet another embodiment shown in FIG. 15c, the apparatus 15 is mounted centrally between the stripping rollers 47a, 47b.

The apparatus 15 arranged on the bale opener 44 can be combined with one or more apparatuses 15 arranged on other machines, such as cleaner 37, card or the like, in order to determine the cleaning performance or efficiency of a cotton blowing room and carding room.

Figure 16:
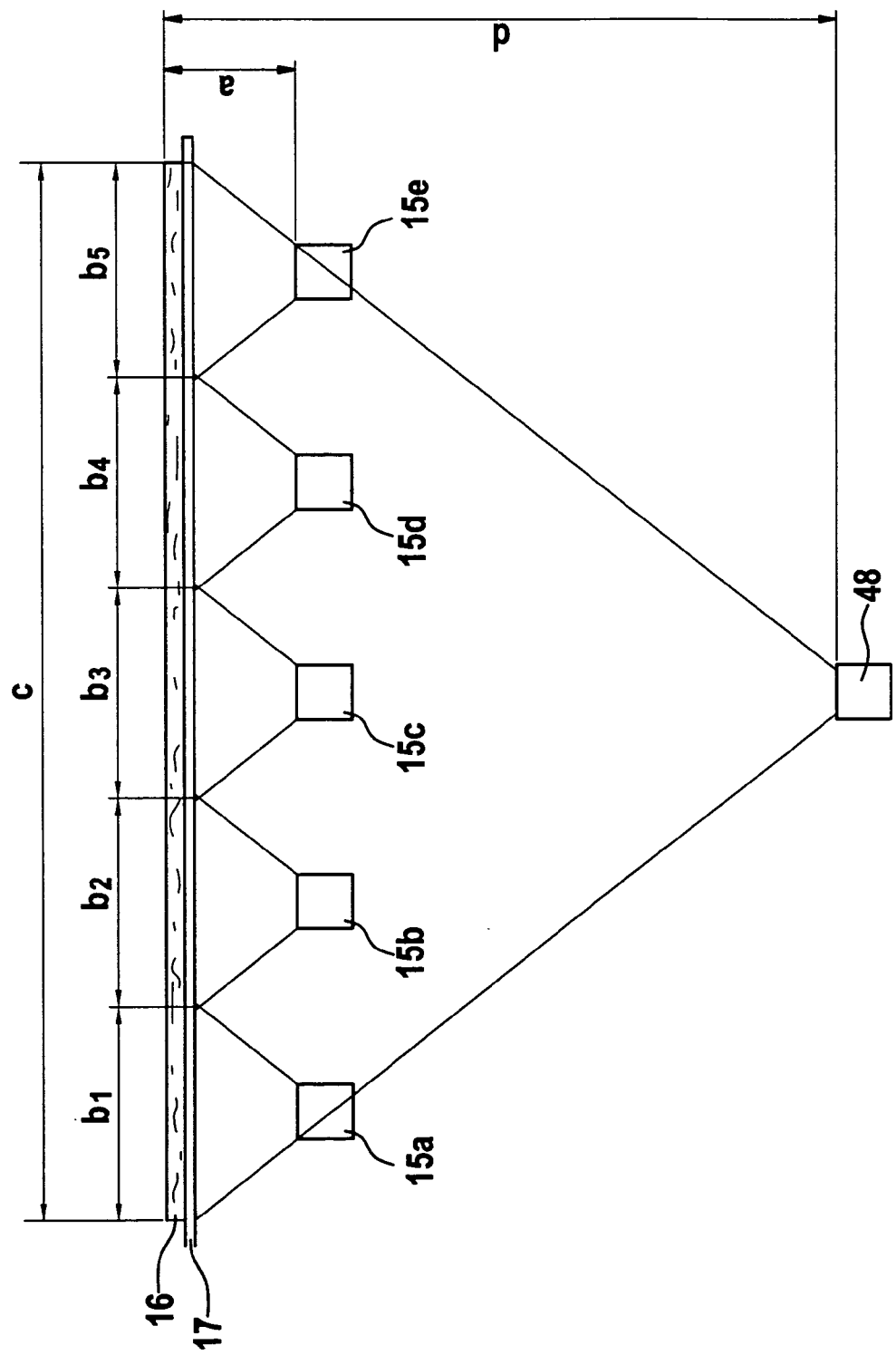
FIG. 16 is a schematic comparison between the known apparatus and an apparatus according to the invention.

As shown in FIG. 16, a fibre web 16 has a width c of 1 m. The known single camera 48, which scans the width c, is arranged a distance d from the fibre web 16. In accordance with the invention, the distance between the image-recognition device and the fibre web 16 is reduced from d to a, providing advantages in terms of space. In order to scan the width c of 1 m, five camera modules 15a to 15e are provided, which scan respective width regions $b_1$ to $b_5$ of 20 cm each. The above schematic example is for illustrative purposes. Compared with the single camera 48, for the same unit of width c the number of cameras 15a to 15e increases as the distance decreases from d to a. Advantageously, a plurality of inexpensive camera modules 15a to 15n is used. The distance a can therefore be reduced. The number of camera modules 15a to 15e and the distance a depend inter alia on the desired image detail corresponding to the width regions $b_1$ to $b_5$ and the resolution. When using CCD cameras having dimensions of about 15×15 mm, the distance a can be, for example, 25 mm. Alternatively, the distance a can be reduced to below 1 mm. For example, the objective 18a can lie adjacent to the window 17.

In accordance with the invention, an arrangement is produced which enables the fleece of a carding machine, or other fibrous material, to be objectively evaluated automatically, continuously and without interruptions. Furthermore, the results obtained are capable of being displayed and further processed automatically.

Several (at least two) small, inexpensive electronic camera modules are mounted across the width of the textile machine. These are so arranged that each one monitors a limited region of the fibrous material, for example, the emerging fleece. The monitoring regions of adjacent modules advantageously have a certain overlap. The necessary illumination is advantageously located directly on the camera modules. The cameras can be matrix cameras or line-scan cameras. The use of a corresponding number (at least two) small camera modules ensures, firstly, that the whole region of the fibrous material to be examined is monitored at the correct time (100% inspection) and, secondly, that the required overall space in a vertical direction is as small as possible. The individual camera modules can all be connected to a central evaluating device and the image information can be processed there. As required, a camera signal evaluation can be carried out by additional upstream evaluating units. Depending on capability, such a unit can evaluate the signals of one or more camera modules. The camera modules can be constructed so that they contain only the indispensable elements, these being, in particular, the objective and image-recognition chip. All other elements, e.g. illumination means, printed circuit board, synchronizer, power supply, device for reading out the individual pixels etc. can be provided centrally and singly for all camera modules simultaneously.

The apparatus according to the invention can also be used on a carding machine for wool. It can be used quite generally for monitoring and checking the fleece of a carding machine or wool carding machine located within or emerging from the machine. The arrangement can also be used to detect foreign fibres or foreign objects and, for example, to provide a report or shut off the machine. Shut-off can be effected, for example, in dependence on the size and type (which can be set beforehand for each set-up) of the detected objects or impurities. The arrangement can also be used to determine the fibre orientation in the in-coming or emerging fleece. It is also possible to use the arrangement to monitor the uniformity ("cloudiness") of the fleece. The arrangement can furthermore be used to detect holes in the fleece or to monitor the fleece form in the marginal zones. By means of the arrangement, the fibrous material circulating on a roller, for example, the cylinder, can also be monitored and examined. In a cleaner, the use of this arrangement enables the degree of contamination of the in-coming or out-going material to be determined. When both sides, the incoming side and the out-going side, are monitored, the effectiveness and cleaning performance of the corresponding machine can automatically be determined and in combination with other elements also automatically influenced. It is also possible to evaluate waste using the arrangement.

For that purpose, it must be integrated in the waste flow so that the latter is directed over or past the arrangement. The camera modules can also be mounted at the individual suction hoods in such a way that a continuous monitoring of the waste is possible. Furthermore, by means of the camera modules it is possible to recognise foreign objects, these being subsequently removed from the system (for example, by blowing out). The arrangement according to the invention can also be used for determining and removing foreign objects from the system (SCFO). The relatively small overall space required here is especially advantageous.

The invention comprises an apparatus for on-line measurement of the proportion of foreign fibres or foreign objects in spinning preparation machines, in which an optical measuring system is integrated at one point before and another point behind the foreign fibre or foreign object separator, the measuring system detecting the proportion of foreign fibres or foreign objects in the material and expressing this as one or more measured values. The measuring system after the foreign fibre or foreign object separator is integrated wholly or partially in the device thereof for detecting the foreign fibres or foreign objects. The measuring system after the foreign fibre or foreign object separator is integrated in the device that is already used in subsequent machines to measure other process parameters. Instead of the measuring system after the foreign fibre or foreign object separator, the measuring system can be integrated in the waste flow thereof. An apparatus is preferably provided for evaluating, displaying and monitoring the data of the measuring systems and for parameterising the foreign fibre or foreign object separator in dependence on the actual material source on hand.

An apparatus of the invention may be in a form suitable for use with any one or more of the forms of fibre structure encountered in spinning preparation processes, for example, any fibre structure encountered from the removal of fibre material from bales by a bale opener to the carding of fibre material, for example, by a carding machine and the formation of a fibre sliver.

What is claimed is:

1. An apparatus on a textile fibre processing machine for inspecting and evaluating textile fibre material, the apparatus comprising an opto-electronic system for scanning the textile fibre material, there being relative movement between the opto-electronic system and the fibre material in a working direction and the fibre material having a working width extending transversely to said working direction, the opto-electronic system comprising two or more partial camera modules which are displaced from one another across the working width of the fibre material and which are in communication with a common image-evaluation device, each partial camera module consisting essentially of an objective in combination with a sensor, the system further comprising remote camera components located remotely from said partial camera modules, said remote camera components being common to each of the two or more partial camera modules and comprising one or more components selected from printed circuit boards, synchronizers, power supplies, and devices for reading individual pixels.

2. An apparatus according to claim 1, in which the opto-electronic system is stationarily arranged and, in use, the fibre material is moving along the working direction.

3. An apparatus according to claim 1, in which a multiplicity of partial camera modules are provided laterally displaced from one another across the working width of the fibre material.

4. An apparatus according to claim 1, in which the partial camera modules are offset from one another in the working direction.

5. An apparatus according to claim 1, in which the partial camera modules are connected to a common evaluation device.

6. An apparatus according to claim 1, in which there are two or more intermediate evaluating devices, each intermediate evaluation device being in communication with a respective partial camera module or group of partial camera modules and the intermediate evaluating devices being in communication with a common evaluation device.

7. An apparatus according to claim 1, which is suitable for maintaining a continuously moving body of sliver.

8. An apparatus according to claim 1, in which the entire width of the fibre material can be monitored simultaneously.

9. An apparatus according to claim 1, in which the opto-electronic system comprises movable opto-electronic sensors.

10. A textile fibre processing machine comprising at least one apparatus according to claim 1.

11. A textile fibre processing machine according to claim 10, comprising first and second said apparatuses.

12. A textile fibre processing machine according to claim 11, in which said first apparatus is arranged to monitor fibre material entering the machine.

13. A textile fibre processing machine according to claim 11, in which said second apparatus is arranged to monitor fibre material emerging from said machine.

14. A textile fibre processing machine according to claim 11, in which data from said second apparatus can be compared with data from said first apparatus.

15. A textile fibre processing machine according to claim 14, in which adjustment of components of the machine can be effected in dependence upon said comparison.

16. A textile fibre processing machine according to claim 10, which is a carding machine.

17. A textile fibre processing machine according to claim 16, in which the apparatus is arranged to monitor fibre that is being transported by a roller of the machine.

18. A textile fibre processing machine according to claim 16, which comprises a said apparatus arranged to examine a fibre web in an outlet region of the machine.

19. A textile fibre processing machine according to claim 10, wherein the machine is an automatic bale opener and cleaner machine.

20. A textile fibre processing machine according to claim 19, in which a said apparatus is arranged to monitor fibre that is being transported by a roller of the machine.

21. A textile fibre processing machine according to claim 10, in which a said apparatus is arranged to monitor waste separated from the fibre material.

22. An apparatus on a spinning machine for inspecting and evaluating textile fibre material having a width, comprising a fixed opto-electronic system which scans the moving fibre material and converts the measured values into electronic signals, the system being in communication with an image-evaluating device (with computer) which evaluates the electronic signals, wherein the opto-electronic system comprises two or more partial camera modules located side by side across the width of the fibre material, each partial camera module consisting essentially of an objective in combination with a sensor, the system further comprising remote camera components located remotely from said partial camera modules, said remote camera components being common to each of the two or more partial camera modules and comprising one or more components selected from printed circuit boards, synchronizers, power supplies, and devices for reading individual pixels.

23. An apparatus for inspecting and evaluating a textile fibre material having a width in which moving opto-electronic sensors scan the stationary fibre material and the measured values are converted into electrical signals, the opto-electronic sensors being in communication with an image-evaluating device (with computer), which evaluates the raw data of the opto-electronic sensors, wherein three or more opto-electronic sensors are provided side by side across the width of the fibre material, wherein each opto-electric sensor consists essentially of an objective in combination with a sensor, the system further comprising remote components located remotely from said optic-electric sensors and common to each of the three or more opto-electric sensors, the remote components comprising one or more components selected from printed circuit boards, synchronizers, power supplies, and devices for reading individual pixels.

* * * * *